(12) United States Patent
Yata et al.

(10) Patent No.: US 10,947,574 B2
(45) Date of Patent: Mar. 16, 2021

(54) METHOD FOR PRODUCING FERMENTED CAROTENOID USING CAROTENOID-PRODUCING BACTERIA OBTAINED BY USING COBALT-CONTAINING CULTURING MEDIUM

(71) Applicant: ENEOS CORPORATION, Tokyo (JP)

(72) Inventors: Tetsuhisa Yata, Tokyo (JP); Hisashi Yoneda, Tokyo (JP); Mitsutoshi Azuma, Tokyo (JP); Kazuaki Hirasawa, Tokyo (JP)

(73) Assignee: ENEOS CORPORATION, Tokyo (JP)

(*) Notice: Subject to any disclaimer, the term of this patent is extended or adjusted under 35 U.S.C. 154(b) by 90 days.

(21) Appl. No.: 16/065,030

(22) PCT Filed: Dec. 27, 2016

(86) PCT No.: PCT/JP2016/088821
§ 371 (c)(1),
(2) Date: Nov. 21, 2018

(87) PCT Pub. No.: WO2017/115774
PCT Pub. Date: Jul. 6, 2017

(65) Prior Publication Data
US 2019/0112628 A1 Apr. 18, 2019

(30) Foreign Application Priority Data
Dec. 28, 2015 (JP) .............................. JP2015-255920

(51) Int. Cl.
*C12P 23/00* (2006.01)
*C12N 1/20* (2006.01)
*C12R 1/01* (2006.01)

(52) U.S. Cl.
CPC ............... *C12P 23/00* (2013.01); *C12N 1/20* (2013.01); *C12R 1/01* (2013.01)

(58) Field of Classification Search
CPC ............ C12P 23/00; C12N 1/20; C12R 1/01
USPC ........................................................ 435/67
See application file for complete search history.

(56) References Cited

U.S. PATENT DOCUMENTS

| | | | |
|---|---|---|---|
| 5,858,761 A | 1/1999 | Tsubokura et al. | |
| 2007/0054351 A1 | 3/2007 | Zhang | |
| 2009/0298146 A1 | 12/2009 | Choi et al. | |
| 2011/0262981 A1 | 10/2011 | Hirasawa et al. | |
| 2013/0012594 A1 | 1/2013 | Hirasawa et al. | |
| 2013/0030218 A1 | 1/2013 | Hirasawa et al. | |

FOREIGN PATENT DOCUMENTS

| | | | |
|---|---|---|---|
| CN | 1392244 | * | 1/2003 |
| CN | 1392244 A | | 1/2003 |
| CN | 103044303 A | | 4/2013 |
| EP | 438182 A1 | | 7/1991 |
| EP | 2157168 A1 | | 2/2010 |
| EP | 2345736 A1 | | 7/2011 |
| JP | H07-046980 A | | 2/1995 |
| JP | H07-079796 A | | 3/1995 |
| JP | H11-069969 A | | 3/1999 |
| JP | 2001-512030 A | | 8/2001 |
| JP | 2006-340676 A | | 12/2006 |
| JP | 2007-097584 A | | 4/2007 |
| JP | 2007-143491 A | | 6/2007 |
| JP | 2007-143492 A | | 6/2007 |
| JP | 2007-244205 A | | 9/2007 |
| JP | 2008-259449 A | | 10/2008 |
| JP | 2011-188795 A | | 9/2011 |
| JP | 2012-139164 A | | 7/2012 |
| JP | 2012-139166 A | | 7/2012 |
| WO | 88/08025 A1 | | 10/1988 |
| WO | 99/06586 A1 | | 2/1999 |
| WO | 2005/118812 A1 | | 12/2002 |
| WO | 2005/118812 A1 | | 12/2005 |
| WO | 2007/093523 A1 | | 8/2007 |
| WO | 2010/04469 A1 | | 1/2010 |
| WO | 2010/044469 A1 | | 4/2010 |
| WO | 2011/122616 A1 | | 10/2011 |

OTHER PUBLICATIONS

Keyhani et al., Cobalt-induced stimulation and inhibition of cytochromes synthesis and extracellular nitrite release in Paracoccus denitrificans, British Library Inside Conferences, (2006), pp. 42-45.*
J. Choi et al., "Optimization of Medium for Astaxanthin Production by *Paracoccus* sp. Using Response Surface Methodology," KSBB Journal, vol. 24, No. 3, Jun. 2009, pp. 321-326.
Extended European Search Report issued in Application No. 16881749.2 dated Nov. 16, 2018.
Buzzini et al., Enzyme and Microbial Technology, (2005), vol. 36, 687-692. (cited in ISR and JPOA).
International Search Report issued in Application No. PCT/JP2016/088821 dated Mar. 21, 2017, with English translation.
Decision to Grant issued in Japanese Application No. 2017-536048 dated Jan. 23, 2018, with English translation.
E. Widmer, "Synthetic advances in the carotenoid field", Pure & Appl. Chem., vol. 57, pp. 741-752, 1985.
E. Widmer et al., Helvetica Chimca Acta, vol. 64, Fase. 7,(1981), pp. 2436-2446.
Lee et al., International Journal of Systematic and Eveolutional Microbiology (2004), 54, 1699-1702.

(Continued)

*Primary Examiner* — Jennifer M. H. Tichy
(74) *Attorney, Agent, or Firm* — McDermott Will & Emery LLP

(57) ABSTRACT

The present invention provides a method for high yield and stable production of carotenoids through microbial culture. The present invention provides a method for culture of carotenoid-producing bacteria, which comprises culturing carotenoid-producing bacteria in a medium containing cobalt or a cobalt salt at a concentration of 0.005 μmol/L to 20 μmol/L.

18 Claims, 3 Drawing Sheets

Specification includes a Sequence Listing.

(56) References Cited

OTHER PUBLICATIONS

Berry et al., International Journal of Systematic and Evolutionary Microbiology (2003), 53, 231-238.
Tsubokura et al., International Journal of Systematic Bacteriology, (1999), 49, 277-282.
Japanese Office Action issued in Application No. 2017-536048 dated Aug. 22, 2017, with English translation.
Decision to Grant issued in Japanese Application No. 2017-536048 dated Jan. 18, 2018, with English translation.
Canadian Office Action issued in Application No. 3,010,090 dated Jul. 17, 2018.
Australian Examination Report issued in Application No. 2016381993 dated Jul. 16, 2018.
Hahnke et al., "An improved medium for the anaerobic growth of Paracoccus denitrificans Pd1222," Frontiers in Microbiology, vol. 5, Article 18, Jan. 2014, pp. 1-9.
Ide et al., "Enhanced production of astaxanthin in *Paracoccus* sp. strain N-81106 by using random mutagenesis and genetic engineering," Biochemical Engineering Journal, 65 (2012) 37-43.
Harker et al., "*Paracoccus marcusii* sp. nov., an orange gram-negative coccus", Int. J. Syst. Bacteriol., vol. 48, Pt. 2, pp. 543-548 (1998).
Takaich et al., "Major carotenoid isolated from Paracoccus schoinia NBRC 100637$^T$ is adonixanthin diglucoside", J. Nat. Prod., vol. 69, No. 12, pp. 1823-1825 (2006).
Tsubokura et al., "*Paracoccus carotinifaciens* sp. nov., a new aerobic gram-negative astaxanthin-producing bacterium", Int. J. Syst. Bacteriol., vol. 49, Pt. 1, pp. 277-282 (1999).

\* cited by examiner

SEQUENCE LISTING

```
<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: Carotenoid-producing bacterial strain E-396
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg gcccagactc     300
ctacgggagg cagcagtggg gaatcttaga caatggggc aaccctgatc tagccatgcc      360
gcgtgagtga tgaaggcctt agggttgtaa agctctttca gctgggaaga taatgacggt     420
accagcagaa gaagccccgg ctaactccgt gccagcagcc gcggtaatac ggaggggct      480 agcgttgttc ggaattactg ggcgtaaagc gcacgtaggc ggactggaaa gtcagaggtg     540
aaatcccagg gctcaacctt ggaactgcct ttgaaactat cagtctggag ttcgagagag     600
gtgagtggaa ttccgagtgt agaggtgaaa ttcgtagata ttcggaggaa caccagtggc     660
gaaggcggct cactggctcg atactgacgc tgaggtgcga aagcgtgggg agcaaacagg     720
```

```
attagatacc ctggtagtcc acgccgtaaa cgatgaatgc cagacgtcgg caagcatgct        780
tgtcggtgtc acacctaacg gattaagcat tccgcctggg gagtacggtc gcaagattaa        840
aactcaaagg aattgacggg ggcccgcaca agcggtggag catgtggttt aattcgaagc        900
aacgcgcaga accttaccaa cccttgacat ggcaggaccg ctggagagat tcagctttct        960
cgtaagagac ctgcacacag gtgctgcatg gctgtcgtca gctcgtgtcg tgagatgttc       1020
ggttaagtcc ggcaacgagc gcaacccacg tccctagttg ccagcaattc agttgggaac       1080
tctatggaaa ctgccgatga taagtcggag gaaggtgtgg atgacgtcaa gtcctcatgg       1140
gccttacggg ttgggctaca cacgtgctac aatggtggtg acagtgggtt aatcccaaa        1200 agccatctca gttcggattg tcctctgcaa ctcgagggca tgaagttgga atcgctagta       1260
atcgcggaac agcatgccgc ggtgaatacg ttcccgggcc ttgtacacac cgcccgtcac       1320
accatgggag ttggttctac ccgacgacgn tgcgctaacc ttcgggggc aggcggccac        1380 ggtaggatca gcgactgggg tgaagtcgta acaaggtagc cgtagggaa cctgcggctg        1440 gatcacctcc tt                                                           1452
```

METHOD FOR PRODUCING FERMENTED CAROTENOID USING CAROTENOID-PRODUCING BACTERIA OBTAINED BY USING COBALT-CONTAINING CULTURING MEDIUM

RELATED APPLICATIONS

This application is a national stage of International Application No. PCT/JP2016/088821, filed Dec. 27, 2016, which claims the benefit of Japanese Application No. 2015-255920, filed on Dec. 28, 2015, the disclosures of which are incorporated in their entirety by reference herein.

TECHNICAL FIELD

The present invention relates to a method for microbiological production of carotenoids by carotenoid-producing bacteria. More specifically, the present invention relates to a method involving fermentation of microorganisms capable of producing carotenoids including astaxanthin, canthaxanthin, zeaxanthin, β-cryptoxanthin, lycopene, β-carotene, adonirubin, adonixanthin, echinenone, asteroidenone and 3-hydroxyechinenone to thereby produce these carotenoids.

BACKGROUND ART

Carotenoids are valuable natural pigments for use as feed additives, food additives, pharmaceutical ingredients or the like. Carotenoids include astaxanthin, canthaxanthin, zeaxanthin, β-cryptoxanthin, lycopene, β-carotene, adonirubin, adonixanthin, echinenone, asteroidenone and 3-hydroxyechinenone. Among them, astaxanthin is useful as a body color improver for farmed fish (e.g., salmon, trout, red sea bream) and also useful as a feed additive such as a color improver for poultry egg yolk. Moreover, natural astaxanthin is of great industrial value as a safe food additive or health food material. As in the case of astaxanthin, adonixanthin and adonirubin are also expected to be used as feed additives, food additives, pharmaceutical ingredients or the like.

Likewise, β-carotene is used as a feed additive, a food additive, a pharmaceutical ingredient or the like, canthaxanthin is used as a feed additive, a food additive, a cosmetic ingredient or the like, and zeaxanthin is used as a food additive, a feed additive or the like. In addition, lycopene, echinenone, β-cryptoxanthin, 3-hydroxyechinenone, asteroidenone and others are also expected to be used as feed additives, food materials or the like. For production of these carotenoids, techniques known for this purpose include chemical synthesis, extraction from naturally occurring products, production through microbial culture, etc.

For chemical synthesis of astaxanthin, conversion from β-carotene (Pure Appl. Chem., 57, 741, 1985 (Non-patent Document 1)) and synthesis from C15 phosphonium salt (Helv. Chim. Acta, 64, 2436, 1981 (Non-patent Document 2)) are known for this purpose. In the case of extraction from naturally occurring products, astaxanthin may be collected by being extracted from fish (e.g., salmon, red sea bream) and crustaceans (e.g., shrimp, crab, krill) because astaxanthin is found therein.

For microbial production of carotenoids, there are reports of culture in green alga *Haematococcus pluvialis* (JP 2007-97584 A (Patent Document 1)), fermentation in red yeast *Phaffia rhodozyma* (JP H11-69969 A (Patent Document 2)), fermentation in bacteria belonging to the genus *Paracoccus* (hereinafter also referred to as "*Paracoccus* sp."), fermentation in bacteria belonging to the genus *Brevundimonas* (JP 2006-340676 A (Patent Document 3)) and fermentation in bacteria belonging to the genus *Erythrobacter* (JP 2008-259449 A (Patent Document 4)). Examples of carotenoid-producing bacteria belonging to the genus *Paracoccus* include strains E-396 and A-581-1 (JP H07-79796 A (Patent Document 5) and International Journal of Systematic Bacteriology (1999), 49, 277-282 (Non-patent Document 3)). Other carotenoid-producing bacteria belonging to the genus *Paracoccus* include *Paracoccus marcusii* strain MH1 (JP 2001-512030 A (Patent Document 6)), *Paracoccus haeundaensis* strain BC74171 (International Journal of Systematic and Evolutionary Microbiology (2004), 54, 1699-1702 (Non-patent Document 4)), *Paracoccus* sp. strain N-81106 (JP 2007-244205 A (Patent Document 7)), *Paracoccus zeaxanthinifaciens* (International Journal of Systematic and Evolutionary Microbiology (2003), 53, 231-238 (Non-patent Document 5)) and *Paracoccus* sp. strain PC-1 (WO2005/118812 (Patent Document 8)), etc.

However, the above techniques for carotenoid production have some problems. For example, carotenoids produced by chemical synthesis would make an unfavorable impression on consumers in terms of safety. Carotenoids extracted from naturally occurring products require remarkably higher production costs than those produced by chemical synthesis. Among microbial production techniques, production through culture of green algae or yeast is disadvantageous not only in low productivity, but also in the difficulty of extracting carotenoids from their cultured products because these microorganisms have rigid cell walls.

In contrast, the production of carotenoids by bacteria belonging to the genus *Paracoccus* is advantageous in terms of their high proliferation rate, high carotenoid productivity, easy extraction of carotenoids from their cultured products, etc., and some reports have been issued for their culture and production methods.

By way of example, JP 2007-143492 A (Patent Document 9) discloses a method involving addition of an iron salt during culture, WO2010/044469 (Patent Document 10) discloses a method using a medium supplemented with amino acids, JP 2011-188795 A (Patent Document 11) discloses a method using a medium supplemented with biotin, and JP 2012-139164 A (Patent Document 12) discloses a method using a medium supplemented with a calcium compound at a concentration of 3.6 mM or higher. However, in carotenoid fermentation in bacteria belonging to the genus *Paracoccus*, details have been unknown as to how their culture and production methods will be affected by the composition of the medium used.

PRIOR ART DOCUMENTS

Patent Documents

Patent Document 1: JP 2007-97584 A
Patent Document 2: JP H11-69969 A
Patent Document 3: JP 2006-340676 A
Patent Document 4: JP 2008-259449 A
Patent Document 5: JP H07-79796 A
Patent Document 6: JP 2001-512030 A
Patent Document 7: JP 2007-244205 A
Patent Document 8: WO2005/118812
Patent Document 9: JP 2007-143492 A
Patent Document 10: WO2010/044469
Patent Document 11: JP 2011-188795 A
Patent Document 12: JP 2012-139164 A Non-Patent Documents Non-patent Document 1: Pure Appl. Chem., 57, 741, 1985
Non-patent Document 2: Helv. Chim. Acta, 64, 2436, 1981
Non-patent Document 3: International Journal of Systematic Bacteriology (1999), 49, 277-282
Non-patent Document 4: International Journal of Systematic and Evolutionary Microbiology (2004), 54, 1699-1702
Non-patent Document 5: International Journal of Systematic and Evolutionary Microbiology (2003), 53, 231-238

SUMMARY OF THE INVENTION

Problem to be Solved by the Invention

During culture of carotenoid-producing bacteria to produce carotenoids therein, the inventors of the present invention have encountered a serious problem in that the productivity of carotenoids greatly varies among culture batches and, in some cases, these bacteria cannot grow at all and thus cannot ensure stable production.

The present invention has been made under these circumstances and aims to provide a method for high yield and stable production of carotenoids through microbial culture.

Means to Solve the Problem

As to the reason why the productivity varies among culture batches, the cause thereof was extremely difficult to find out because there were various possible factors including improper aeration and stirring, temperature fluctuations, pH fluctuations, abnormal performance of dissolved oxygen electrodes, activity fluctuations among seed bacteria, variations among lots of medium ingredients, fluctuations of trace components in water, loss of nutrient sources and generation of inhibitory substances upon medium sterilization, effects from magnetism and vibration, electrical stimulation, contamination with various germs, contamination with inhibitory substances from the equipment used, etc.

As a result of expending great amounts of effort and time for extensive and intensive studies and also repeating many various efforts to solve the problem stated above, the inventors of the present invention have found that cobalt in a medium is an important factor for the growth of carotenoid-producing bacteria and for the production of carotenoids, so that microorganisms cannot grow when the cobalt concentration in a medium is too low, while microorganisms also cannot grow when the cobalt concentration is too high. Further, the inventors of the present invention have found out that in conventional techniques, when cobalt introduced into a medium as a trace contaminant from, e.g., medium ingredients, water or metallic parts of the fermentation equipment is present in an appropriate amount, carotenoid-producing bacteria grow well and can be cultured to produce carotenoids at high levels, whereas when the amount of cobalt as a contaminant does not reach an appropriate amount, these bacteria cannot be cultured and hence stable production is impossible.

Moreover, the inventors of the present invention have found that the amount of cobalt required for culture is a trace amount and that there is a concentration range suitable for culture, and therefore have confirmed that the concentration of cobalt in a medium is a very important factor in the growth of carotenoid-producing bacteria and the production of carotenoids, of which nobody had been aware in prior art techniques.

Namely, the inventors of the present invention have elucidated, ahead of others, that cobalt is a nutrient essential for the growth of carotenoid-producing bacteria and the production of carotenoids, and also there is an appropriate range in its concentration. These findings led to the completion of a method for microbiological production of carotenoids by carotenoid-producing bacteria according to the present invention, which solved the problems associated with their production and enabled the stable microbial production of carotenoids.

The present invention has the following features.

(1) A method for culture of highly carotenoid-producing bacteria, which comprises culturing carotenoid-producing bacteria in a medium containing cobalt or a cobalt salt at a concentration of 0.005 µmol/L to 20 µmol/L.

(2) A method for preparation of highly carotenoid-producing bacteria, which comprises culturing carotenoid-producing bacteria in a medium containing cobalt or a cobalt salt at a concentration of 0.005 µmol/L to 20 µmol/L.

(3) A method for production of carotenoids, which comprises culturing carotenoid-producing bacteria in a medium containing cobalt or a cobalt salt at a concentration of 0.005 µmol/L to 20 µmol/L, and collecting carotenoids from the resulting cultured product.

(4) The method according to any one of (1) to (3) above, wherein the concentration of cobalt or a cobalt salt in the medium is 0.005 µmol/L to 8 µmol/L.

(5) The method according to any one of (1) to (4) above, wherein the carotenoids comprise at least one selected from the group consisting of astaxanthin, canthaxanthin, zeaxanthin, PI-cryptoxanthin, lycopene, β-carotene, adonirubin, adonixanthin, echinenone, asteroidenone and 3-hydroxyechinenone.

(6) The method according to any one of (1) to (5) above, wherein the carotenoid-producing bacteria are those belonging to the genus *Paracoccus, Brevundimonas* or *Erythrobacter*.

(7) The method according to any one of (1) to (6) above, wherein the carotenoid-producing bacteria are those comprising DNA which corresponds to 16S ribosomal RNA and whose nucleotide sequence shares a homology of 95% or higher with the nucleotide sequence shown in SEQ ID NO: 1.

(8) The method according to any one of (1) to (7) above, wherein the carotenoid-producing bacteria are those of the strain E-396 (FERM BP-4283) or the strain A-581-1 (FERM BP-4671) or a mutant strain thereof.

(9) Highly carotenoid-producing bacteria prepared by the method according to any one of (2) and (4) to (8) above.

(10) Highly carotenoid-producing bacteria, which contain carotenoids in an amount of at least 36 mg/g in their dry microbial cells.

(11) Highly carotenoid-producing bacteria, which contain cobalt.

Effects of the Invention

The present invention enables the provision of carotenoid-producing bacteria or a method for production of carotenoids, which stably achieves high productivity without being affected by the composition of the medium used, manufacturers of water or other ingredients and their grade, lot and manufacturing place, materials constituting the fermentation equipment used and its manufacturing place, etc.

DESCRIPTION OF EMBODIMENTS

Figure 1:
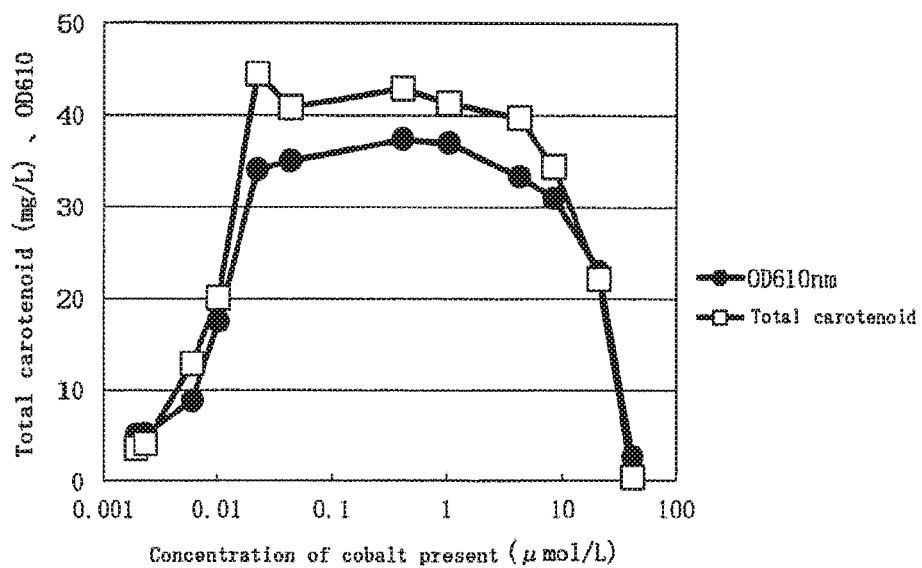
FIG. 1 shows the relationship between the concentration of cobalt present in a medium and microbial cell growth OD610 or total carotenoid production level.

The present invention will be further described in more detail below. The scope of the present invention is not limited by the following description, and any embodiments other than those illustrated below may also be carried out with appropriate modifications without departing from the spirit of the present invention.

It should be noted that the numerical values shown in the tables in this specification may also be expressed differently, e.g., by changing the number of significant figures or the number of digits to be rounded off (e.g., the last digit, the last two digits) as appropriate for the experiments conducted. For this reason, there are some cases where the numerical value shown as a total value is not the same as the sum of individual numerical values.

The present invention relates to a method for production of carotenoids by stably culturing carotenoid-producing bacteria, and this method is characterized in that cobalt or a cobalt salt is present in a medium at a concentration within a predetermined range.

The method of the present invention allows stable culture of carotenoid-producing bacteria and stable production of carotenoids at high levels.

Bacteria for use in the present invention are not limited in any way as long as they are carotenoid-producing bacteria, as exemplified by bacteria belonging to the genera *Paracoccus, Brevundimonas* and *Erythrobacter*.

Preferred for use are bacteria belonging to the genus *Paracoccus*, bacteria belonging to the genus *Brevundimonas* or bacteria belonging to the genus *Erythrobacter*, and more preferred for use are bacteria belonging to the genus *Paracoccus*. The genera *Paracoccus, Erythrobacter* and *Brevundimonas* are all classified as phylum Proteobacteria, class Alphaproteobacterta, and hence they have a commonality in terms of bacterial taxonomy. For this reason, bacteria belonging to these genera can be used in the present invention.

Among bacteria belonging to the genus *Paracoccus*, preferred for use are *Paracoccus carotinifaciens, Paracoccus marcusti, Paracoccus haeundaensis* and *Paracoccus zeaxranthinifaciens*, with *Paracoccus carotinifaciens* being particularly preferred for use. Actual strains of bacteria belonging to the genus *Paracoccus* may be exemplified by *Paracoccus carotinifaciens* strain E-396 and *Paracoccus* sp. strain A-581-1 (FERM BP-4671), and mutant strains thereof are also preferred for use in the present invention.

Carotenoid-producing bacteria belonging to the genus *Erythrobacter* may be exemplified by *Erythrobacter* JPCC M sp. (JP 2008-259452 A), *Erythrobacter* JPCC O sp. (JP 2008-259449 A) and so on.

Carotenoid-producing bacteria belonging to the genus *Brevundimonas* may be exemplified by *Brevundimonas* strain SD212 (JP 2009-27995 A), *Brevundimonas* FERM strains P-20515 and P-20516 (JP 2006-340676 A), *Brevundimonas vesicularis* (Gene, Vol. 379, p. 101-108, 1 Sep. 2006) and so on.

Moreover, carotenoid-producing bacteria preferred for use are those sharing high homology in the nucleotide sequence of DNA corresponding to 16S ribosomal RNA with respect to the nucleotide sequence of the strain E-396 shown in SEQ ID NO: 1. The nucleotide sequence homology intended here is preferably 95% or higher, more preferably 96% or higher, even more preferably 97% or higher, particularly preferably 98% or higher, and most preferably 99% or higher.

The nucleotide sequence of DNA corresponding to 16S ribosomal RNA is intended to mean a nucleotide sequence containing T (thymine) in place of U (uracil) in the nucleotide sequence of 16S ribosomal RNA.

Microbial classification based on the homology of the nucleotide sequence of this 16S ribosomal RNA has become mainstream in recent years. Conventionally used microbial classifications are based on previously known microbiological properties (e.g., motility, auxotrophy, sugar assimilability) and hence may cause misclassification of microorganisms in some cases when a spontaneous mutation has induced a phenotypic change or the like. In contrast, the nucleotide sequence of 16S ribosomal RNA is genetically very stable, so that classification based on the homology of this RNA ensures remarkably improved confidence in the classification results when compared to conventionally used classifications.

The nucleotide sequence of 16S ribosomal RNA in *Paracoccus carotinifaciens* strain E-396 shares a homology of 99.7%, 99.7%, 99.6%, 99.4%, 95.7% and 95.4% with the nucleotide sequences of 16S ribosomal RNA in other carotenoid-producing bacteria, i.e., *Paracoccus marcusil* strain DSM 11574, *Paracoccus* sp. strain N-81106, *Paracoccus haeundaensis* strain BC 74171, *Paracoccus* sp. strain A-581-1, *Paracoccus zeaxanthinifaciens* strain ATCC 21588 and *Paracoccus* sp. strain PC-I, respectively, which indicates that they are taxonomically very closely related strains. Thus, these strains appear to constitute a group of carotenoid-producing bacteria. For this reason, these strains are preferred for use in the present invention and allows efficient production of carotenoids.

In the present invention, it is also possible to use a mutant strain engineered to have improved productivity of carotenoids. Examples of such a mutant strain include those engineered to highly produce astaxanthin (JP 2001-95500 A), those engineered to selectively produce canthaxanthin at high level (JP 2003-304875 A), those engineered to selectively produce zeaxanthin and β-cryptoxanthin at high levels (JP 2005-87097 A) and those engineered to selectively produce lycopene (JP 2005-87100 A).

Such a mutant strain engineered to have improved productivity of carotenoids may be obtained by mutagenesis and screening. Any technique may be used for mutagenesis as long as it induces a mutation(s). For example, it is possible to use chemical techniques using a mutagen such as N-methyl-N'-nitro-N-nitrosoguanidine (NTG) or ethyl methanesulfonate (EMS), physical techniques such as ultraviolet irradiation and X-ray irradiation, or biological techniques based on gene recombination or transposon, etc. Although bacteria to be mutated are not limited in any way, they are preferably carotenoid-producing bacteria. Alternatively, such mutant strains may be generated as a result of spontaneous mutations.

Screening for mutant strains may be accomplished in any manner, for example, by observing the color tone of colonies on agar medium to select a desired mutant strain, or alternatively, by culturing mutant strains in test tubes, flasks, fermenters or the like to select a desired mutant strain by carotenoid pigment analysis using absorbance, high performance liquid chromatography, thin-layer chromatography, etc.

Such mutagenesis and screening steps may be conducted once, or alternatively, may be repeated twice or more, for example, such that mutant strains are obtained by mutagenesis and screening, and the resulting mutant strains are further subjected to mutagenesis and screening to thereby obtain a mutant strain with improved productivity.

The strain E-396 listed as an example of carotenoid-producing bacteria for use in the present invention has been internationally deposited with the International Patent Organism Depositary, the National Institute of Advanced Industrial Science and Technology in Japan, as shown below.

International Deposition Authority: International Patent Organism Depositary, National Institute of Advanced Industrial Science and Technology (former name: National Institute of Bioscience and Human-Technology, Agency of Industrial Science and Technology, Ministry of International Trade and Industry) Central 6, 1-1-1 Higashi, Tsukuba-shi, Ibaraki 305-8566, Japan Label for identification: E-396
Accession No.: FERM BP-4283
Date of original deposition: Apr. 27, 1993

Likewise, the strain A-581-1 listed as another example of carotenoid-producing bacteria for use in the present invention has been internationally deposited with the above depositary, as shown below.

Label for identification: A-581-1
Accession No.: FERM BP-4671
Date of original deposition: May 20, 1994

In the present invention, the above carotenoid-producing bacteria allow stable production of carotenoids at high levels when cultured in a medium containing cobalt or a cobalt salt at a predetermined concentration.

Carotenoids to be produced are not limited in any way, but examples include astaxanthin, canthaxanthin, zeaxanthin, β-cryptoxanthin, lycopene, β-carotene, adonirubin, adonixanthin, echinenone, asteroidenone or 3-hydroxyechinenone. Preferred is astaxanthin, canthaxanthin, zeaxanthin or β-cryptoxanthin, and more preferred is astaxanthin or zeaxanthin. These carotenoids may be produced, either alone or in combination, in the present invention.

The method for culturing the above bacteria in the present invention will be described below.

The present invention relates to a method for culturing carotenoid-producing bacteria in a medium containing cobalt or a cobalt salt at a predetermined concentration.

In the present invention, cobalt or a cobalt salt may be added to a medium and contained therein at a predetermined concentration in any manner, for example, preferably by adding one or more cobalt compounds selected from cobalt chloride, cobalt nitrate, cobalt formate, cobalt acetate, cobalt oxide, cobalt bromide, cobalt carbonate, cobalt sulfate, cobalt naphthenate, cobalt oleate, cobalt stearate, cobalt thiocyanate, cobalt powder, cyanocobalamin and so on to a medium at a concentration within a predetermined range. These cobalt compounds may be in either anhydride or hydrate form. Such a cobalt compound is preferably added to a medium during its preparation stage before initiation of culture, but may be added once, sequentially or continuously after initiation of culture.

In another embodiment, a medium ingredient containing cobalt as a trace contaminant may be added to give a cobalt concentration within a predetermined range. Possible medium ingredients containing cobalt as a trace contaminant may be exemplified by corn steep liquor, Pharmamedia, soybean meal, soybean flour, peanut meal, soy peptone, distillers's solubles, dry yeast, yeast extract, glucose, sucrose, molasses, iron salts, manganese salts, copper salts, zinc salts, molybdenum salts, nickel salts, selenium salts, phosphate salts, magnesium salts, calcium salts, water and so on. These medium ingredients may be added, either alone or in combination, to give a cobalt concentration within a predetermined range. In this embodiment, the cobalt content in medium ingredients may be controlled as appropriate, because the amount of cobalt contained in medium ingredients may vary depending on their manufacturer, lot, manufacturing place, etc. Such a medium ingredient containing cobalt as a trace contaminant is preferably added to a medium during its preparation stage before initiation of culture, but may be added once, sequentially or continuously after initiation of culture.

In yet another embodiment, fermentation equipment made of cobalt-containing material may be used for culture such that cobalt is allowed to dissolve within a predetermined cobalt concentration range. The use of fermentation equipment whose spinner shaft, spinner shaft bearing and/or sealing member is made of a cobalt-containing super alloy, from which cobalt is allowed to dissolve, is also included in this embodiment. In this embodiment, the cobalt concentration in a medium may be analyzed and controlled as appropriate, because the amount of cobalt dissolved may vary depending on the condition of equipment, etc., so that too small an amount of cobalt is not sufficient to serve as a nutrient source, while too large an amount of cobalt inhibits production.

It is also preferable to combine two or more of the above embodiments, i.e., addition of a cobalt compound, addition of a medium ingredient containing cobalt as a trace contaminant, and addition of cobalt dissolved from fermentation equipment made of cobalt-containing material.

As to the timing of adding a cobalt compound, this compound may be added to a seed medium such that cobalt brought from the seed medium is within a predetermined concentration range in a production medium used at the final stage, or cobalt may be added to both a seed medium and a production medium used at the final stage such that cobalt is within a predetermined concentration range in the production medium used at the final stage, or alternatively, the cobalt compound may be added to a medium used at the final stage of culture.

In the present invention, it was found that the growth of microorganisms and the production of carotenoids were not successful at either too low or too high a concentration of cobalt or a cobalt salt contained in the medium. This finding would be because too low a concentration of cobalt is not sufficient to serve as a nutrient source and because too high a concentration of cobalt inhibits the growth of microorganisms and the production of carotenoids.

The lower limit concentration of cobalt or a cobalt salt in the medium is preferably 0.005 µmol/L or higher, 0.006 µmol/L or higher, more preferably 0.01 µmol/L or higher, and even more preferably 0.02 µmol/L or higher. The upper limit concentration is preferably 20 µmol/L or lower, more preferably 10 µmol/L or lower, 9 µmol/L or lower, 8 µmol/L or lower, 7 µmol/L or lower, 6 µmol/L or lower, 5 µmol/L or lower, even more preferably 4 µmol/L or lower, 3 µmol/L or lower, 2 µmol/L, and most preferably 1 µmol/L or lower. In the present invention, the above upper and lower limit concentrations may be selected as appropriate to achieve the cobalt concentration range required for culture, for example, the range of 0.005 µmol/L to 20 µmol/L, 0.006 µmol/L to 20 µmol/L, 0.01 µmol/L to 8 µmol/L, 0.02 µmol/L to 8 µmol/L, 0.02 µmol/L to 7 µmol/L, 0.02 µmol/L to 6 µmol/L, 0.02 µmol/L to 1 µmol/L, etc. However, the above ranges are listed for illustrative purposes only, and the cobalt concentration range is not limited to these ranges.

The medium for carotenoid production to be used for culture in the present invention is a medium containing a predetermined concentration of cobalt or a cobalt salt, but may further be supplemented with any ingredients, in addition to cobalt, as long as they allow carotenoid-producing bacteria to grow and produce carotenoids. Such a medium supplemented with additional ingredients is not limited in any way, but preferred for use is a medium containing a carbon source, a nitrogen source, inorganic salts and optionally vitamins, etc.

Examples of a carbon source include sugars (e.g., glucose, sucrose, lactose, fructose, trehalose, mannose, mannitol and maltose), organic acids (e.g., acetic acid, fumaric acid, citric acid, propionic acid, malic acid, malonic acid and pyruvic acid), alcohols (e.g., ethanol, propanol, butanol, pentanol, hexanol, isobutanol and glycerol), and fats or oils (e.g., soybean oil, rice bran oil, olive oil, corn oil, sesame oil and linseed oil). Among them, glucose or sucrose is preferred for use. These carbon sources may be used either alone or in combination. The amount to be added to the medium before culture (initial medium) will vary depending on the type of carbon source and may be adjusted as appropriate. It is usually 1 to 100 g, preferably 2 to 50 g, per liter of the medium. Moreover, such carbon sources are not only added to the initial medium, but also may preferably be further supplied sequentially or continuously during culture.

Examples of a nitrogen source include inorganic salts such as ammonium salts (e.g., ammonium nitrate, ammonium sulfate, ammonium chloride, ammonium phosphate), nitrate salts (e.g., potassium nitrate), ammonia and urea, which may be used either alone or in combination. The amount to be added will vary depending on the type of nitrogen source and may be adjusted as appropriate. It is usually 0.1 g to 20 g, preferably 0.2 to 10 g, per liter of the medium.

Likewise, examples of an organic nitrogen source include corn steep liquor (including filtered corn steep liquor), Pharmamedia, soybean meal, soybean flour, peanut meal, soy peptone, distillers's solubles, dry yeast, yeast extract, casamino acid, glutamic acid, aspartic acid and so on, which may be used either alone or in combination. The concentration to be added will vary depending on the type of nitrogen source and may be adjusted as appropriate. It is usually 0 to 80 g/L, preferably 1 to 30 g/L.

Such inorganic and organic nitrogen sources are normally added to the initial medium, but preferably may also be further supplied sequentially or continuously during culture.

Examples of inorganic salts include phosphate salts (e.g., potassium dihydrogen phosphate, dipotassium hydrogen phosphate, disodium hydrogen phosphate), magnesium salts (e.g., magnesium sulfate, magnesium chloride), iron salts (e.g., iron sulfate, iron chloride), calcium salts (e.g., calcium chloride, calcium carbonate), sodium salts (e.g., sodium carbonate, sodium chloride), manganese salts (e.g., manganese sulfate), copper salts (e.g., copper sulfate), zinc salts (e.g., zinc sulfate), molybdenum salts (e.g., sodium molybdate), nickel salts (e.g., nickel sulfate), selenium salts (e.g., sodium selenite), tungsten salts (e.g., sodium tungstate), aluminum salts (e.g., aluminum chloride), chromium salts (e.g., chromium chloride), boric acid and potassium iodide, which may be used either alone or in combination. The amount to be added will vary depending on the type of inorganic salt and may be adjusted as appropriate. It is usually 0.0001 to 15 g per liter of the medium. A preferred concentration is 0.02 to 15 g/L for phosphate salts, magnesium salts, calcium salts, sodium salts and iron salts, and is 0.1 to 15 mg/L for manganese salts, copper salts, zinc salts, molybdenum salts, nickel salts, selenium salts, tungsten salts, aluminum salts, chromium salts, boric acid, potassium iodide and so on. Such inorganic salts are normally added to the initial medium, but may also be further supplied sequentially or continuously during culture.

Examples of vitamins available for use include cyanocobalamin, riboflavin, pantothenic acid, pyridoxine, thiamine, ascorbic acid, folic acid, niacin, p-aminobenzoic acid, biotin, inositol, choline and so on. The ratio to be added will vary depending on the type of vitamin and may be adjusted as appropriate. It is usually 0.001 to 1000 mg, preferably 0.01 to 100 mg, per liter of the medium. Such vitamins are normally added to the initial medium, but may also be further supplied sequentially or continuously during culture.

In the present invention, a defoaming agent may preferably be used to avoid bubbling of the culture solution. Such a defoaming agent may be of any type as long as it has the ability to prevent bubble formation or to break the bubbles formed and is also less inhibitory against the intended producing bacteria. Examples include alcohol-based defoaming agents, polyether-based defoaming agents, ester-based defoaming agents, fatty acid-based defoaming agents, silicon-based defoaming agents, sulfonate-based defoaming agents and so on. The amount to be added will vary depending on the type of defoaming agent and may be adjusted as appropriate. It is usually 0.01 g to 10 g per liter of the medium.

Such a defoaming agent is normally added to the initial medium before sterilization, and may further be added continuously or intermittently during culture. For addition during culture, such a defoaming agent may be automatically added upon detection of bubbles with a sensor, or may be added at given time intervals with a programmed timer, or may be added in response to the growth rate in admixture with any component to be fed, e.g., a carbon source, a nitrogen source or a pH adjuster, by way of example. The defoaming agent added to the initial medium and the defoaming agent added to the culture solution during culture may be either of the same or different type, depending on the intended effect.

In the present invention, the initial pH of the medium is adjusted to 2 to 12, preferably 6 to 9, more preferably 6.5 to 8.0. It is preferable to also maintain the medium pH within the above range during culture. Examples of a pH adjuster include aqueous sodium hydroxide, aqueous potassium hydroxide, aqueous sodium carbonate, aqueous ammonia, ammonia gas, aqueous sulfuric acid, or any mixture thereof.

In the present invention, the medium is sterilized before use in bacterial culture. Sterilization may be accomplished as appropriate by those skilled in the art. For example, the medium in an appropriate container may be sterilized by heating in an autoclave. Alternatively, the medium may be sterilized by filtration through a sterile filter.

In the present invention, carotenoid-producing bacteria are inoculated into the medium prepared as above and cultured under predetermined conditions. Inoculation may be accomplished as follows: strains are grown as appropriate by seed culture in test tubes, flasks or fermenters and the resulting cultured products are each added to the medium for carotenoid production. Any medium may be used for seed culture as long as it is a medium allowing carotenoid-producing bacteria to grow well, but the medium should contain the minimum amount of cobalt or a cobalt salt required for growth.

Culture is conducted in an appropriate culture vessel. Such a culture vessel may be selected as appropriate depending on the culture volume and is exemplified by test tubes, flasks, fermenters, etc.

The culture temperature is set to 15° C. to 40° C., preferably 20° C. to 35° C., more preferably 25° C. to 32° C., and culture is conducted under aerobic conditions for usually 1 to 18 days, preferably 2 to 12 days, more preferably 3 to 8 days. Culture under aerobic conditions include, for example, shaking culture or aeration spinner culture, during which the dissolved oxygen concentration is preferably controlled to be within a constant range. The dissolved oxygen concentration may be controlled, for example, by changing the number of spinner rotations, the aeration volume, the internal pressure, etc. The dissolved oxygen concentration is controlled to be preferably 0.3 to 10 ppm, more preferably 0.5 to 7 ppm, and even more preferably 1 to 5 ppm.

In the present invention, after culture of carotenoid-producing bacteria, their cell counts may be determined by OD measurement. Likewise, carotenoids in the cultured product obtained by culture of carotenoid-producing bacteria or carotenoids collected from the cultured product may be quantified by high performance liquid chromatography. Once carotenoid-producing bacteria have been cultured as described above, carotenoids can be collected from the resulting cultured product.

Such a cultured product may be exemplified by a culture solution, a culture supernatant, a concentrated microbial cell suspension, wet microbial cells, dry microbial cells, a microbial cell lysate, etc. A culture supernatant may be prepared from a culture solution by centrifugation or filtration to remove microbial cells from the culture solution. A concentrated microbial cell suspension may be obtained from a culture solution upon concentration by centrifugation or filter filtration. Wet microbial cells may be obtained from a culture solution by centrifugation or filtration. Dry microbial cells may be obtained from wet microbial cells or a concentrated microbial cell suspension upon drying in a standard manner. The carotenoid-containing dry microbial cells thus obtained may be used directly as feed additives.

The resulting dry microbial cells contain carotenoids in an amount of at least 36 mg/g, e.g., 36 mg/g, 37 mg/g, 38 mg/g, 39 mg/g or 40 mg/g. The amount of carotenoids contained in dry microbial cells will vary depending on the type of microbial cells used, but these dry microbial cells contain carotenoids in an amount of for example, 36 mg/g to 50 mg/g, more preferably 36 mg/g to 45 mg/g. Bacteria containing such an amount of carotenoids also fall within the present invention. Accordingly, the present invention provides highly carotenoid-producing bacteria (e.g., bacteria belonging to the genus *Paracoccus, Brevundimonas* or *Erythrobacter*) containing at least 36 mg/g of carotenoids in their dry microbial cells.

In the present invention, any technique may be used to collect carotenoids from the above cultured product as long as it allows stable and efficient collection of carotenoids. Such a technique may be selected as appropriate from among extraction and purification techniques known to those skilled in the art. Alternatively, the above cultured product may be used as a carotenoid-containing composition in the present invention.

Prior to extraction, the cultured product may be subjected to one or more treatments selected from chemical treatments with alkaline reagents, surfactants or the like, biochemical treatments with lytic enzymes, lipolytic enzymes, proteolytic enzymes or the like, or physical treatments such as ultrasonication or homogenization.

For example, when carotenoids are extracted from the cultured product, any solvent may be used for extraction and washing purposes, including lower alcohols (e.g., methanol, ethanol, isopropanol), acetone, tetrahydrofuran, methyl ethyl ketone, methyl isobutyl ketone, dichloromethane, chloroform, dimethylformamide, dimethyl sulfoxide and so on.

To minimize oxidation of carotenoids during the extraction step, the cultured product may be treated in an atmosphere of an inert gas such as nitrogen gas. Likewise, an antioxidant used in pharmaceutical preparations or food products may also be selected and added to the extraction solvent. Alternatively, these treatments may be combined for this purpose. In addition, to minimize light-induced degradation of carotenoids, the cultured product may be treated under light shielding conditions.

The extract thus obtained may be used directly as a carotenoid fraction or may further be purified before use.

Any technique may be used to separate bacterial cells or others remaining in the extract after the extraction step, but filter filtration, centrifugation, decantation or the like may be used for this purpose.

To obtain carotenoid precipitates from the extract, techniques commonly used for this purpose include concentration under heating and/or reduced pressure, as well as crystallization. Alternatively, carotenoid pigments may also be separated, without being concentrated, by precipitation at low temperature or by precipitation with acid or alkaline agents or with various salts. For industrial use, crystallization is desired.

The resulting carotenoid precipitates may optionally be suspended and stirred using a small volume of a solvent (e.g., lower alcohol) for washing purposes. Washing procedures are not limited in any way, and practically preferred procedures include those in which precipitates are collected by filtration after being suspended and stirred, or those in which a solution is passed from above through precipitates.

The cultured product, extract or purified product obtained as described above may be used as a carotenoid fraction, either alone or in admixture at any ratio.

EXAMPLES

The present invention will be further described in more detail by way of the following illustrative examples, which are not intended to limit the scope of the present invention.

In the following examples, carotenoids were quantified by high performance liquid chromatography (HPLC) as follows.

Two columns of Inertsil SIL-100A, 5 μm (φ4.6 mm×250 mm) (GL Sciences Inc., Japan) were connected together for use as a column. For elution, a mixed solution of n-hexane, tetrahydrofuran and methanol (40:20:1) serving as a mobile phase was passed through the column at a flow rate of 1.0 mL per minute at a constant temperature around room temperature. For measurement, samples were each dissolved in tetrahydrofuran and diluted 100-fold with the mobile phase, and 20 μL aliquots of the resulting dilutions were injected into the column. The column eluates were detected at a wavelength of 470 nm. As a standard for quantification, astaxanthin (SIGMA, Cat. No. A9335) was used. The astaxanthin concentration of the standard solution was determined using the following equation after measuring the absorbance (A) of the standard solution at 477 nm and the area percentage % (B) of the astaxanthin peak in HPLC analysis under the above conditions.

$$\text{Astaxanthin concentration(mg/L)}=A/2150 \times B \times 100$$

Example 1

A medium of the following composition (sucrose 30 g/L, corn steep liquor 30 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture. The ingredients used to prepare the test tube medium for seed culture were obtained from lots where microbial cells had been confirmed to grow well.

Subsequently, a medium of the following composition (glucose 30 g/L, filtered corn steep liquor 30 g/L, ammonium sulfate 1.5 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, silicon-based defoaming agent 0.2 g/L) was dispensed in 7.2 ml volumes into cotton-plugged test tubes having an inner diameter of 18 mm to prepare 5 test tubes containing a test tube medium for production. The ingredients used to prepare the test tube medium for production were obtained from lots where microbial cells had been confirmed not to grow well.

Among the above test tubes for production, the first test tube (test tube 1) was supplemented with 0.8 ml of a mixed aqueous solution of trace metals which had been prepared such that their respective final concentrations in the medium were those indicated in Table 1 (cobalt chloride hexahydrate 0.1 mg/L=0.42 μmol/L), the second test tube (test tube 2) was supplemented with 0.8 ml of a mixed aqueous solution of nucleic acids to give the respective concentrations indicated in Table 2, the third test tube (test tube 3) was supplemented with 0.8 ml of a mixed aqueous solution of vitamins to give the respective concentrations indicated in Table 3, the fourth test tube (test tube 4) was supplemented with 0.8 ml of an aqueous solution of trisodium citrate dihydrate to give a concentration of 3 g/L, and the fifth test tube (test tube 5) was supplemented with 0.8 ml of ion exchanged water. The medium in each test tube was adjusted to pH 7.2 with aqueous sodium hydroxide or aqueous sulfuric acid, and then sterilized in an autoclave at 121° C. for 20 minutes.

TABLE 1

| Ingredient | Concentration added per medium (final concentration mg/L) |
| --- | --- |
| Sodium molybdate dihydrate | 1 |
| Manganese sulfate pentahydrate | 1 |
| Sodium tungstate | 1 |
| Zinc sulfate heptahydrate | 1 |
| Nickel sulfate hexahydrate | 1 |
| Copper sulfate pentahydrate | 1 |
| Boric acid | 1 |
| Potassium iodide | 1 |
| Sodium selenate | 0.1 |
| Cobalt chloride hexahydrate | 0.1 |
| Aluminum (III) chloride hexahydrate | 0.1 |
| Chromium (III) chloride hexahydrate | 0.1 |

TABLE 2

| Ingredient | Concentration added per medium (final concentration g/L) |
| --- | --- |
| Thymidine | 0.5 |
| Uridine | 0.5 |
| Cytosine | 0.5 |
| Adenosine | 0.5 |
| Guanosine | 0.5 |

TABLE 3

| Ingredient | Concentration added per medium (final concentration mg/L) |
| --- | --- |
| Riboflavin | 10 |
| Calcium pantothenate | 10 |
| Pyridoxine hydrochloride | 10 |
| Ascorbic acid | 10 |
| Myo-inositol | 10 |
| Choline | 10 |
| Thiamine hydrochloride | 1 |
| Niacin | 1 |
| Folic acid | 1 |
| Cyanocobalamin | 1 |
| Biotin | 1 |

*Paracoccus carotinifaciens* strain E-396 (FERM BP-4283) was inoculated into the test tube medium for seed culture and then cultured under shaking at 28° C. for 2 days at 300 spm. The resulting culture solution was then inoculated in 0.05 ml volumes into the 5 types of test tube media for production and cultured under shaking at 28° C. for 4 days at 300 spm.

When microbial cell growth in each culture solution was determined by OD610 (optical density at 610 nm), only the test tube supplemented with trace metals was found to show good growth among the 5 types of test tube media for production (Table 4).

TABLE 4

| | Ingredient added | OD610 |
|---|---|---|
| Test tube 1 | Trace metals | 34 |
| Test tube 2 | Nucleic acids | 6 |
| Test tube 3 | Vitamins | 6 |
| Test tube 4 | Sodium citrate | 4 |
| Test tube 5 | Ion exchanged water | 5 |

Example 2

The same procedure as shown in Example 1 was repeated to prepare a test tube medium for seed culture. Subsequently, a medium of the following composition (glucose 30 g/L, filtered corn steep liquor 30 g/L, ammonium sulfate 1.5 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, silicon-based defoaming agent 0.2 g/L) was dispensed in 7.2 ml volumes into cotton-plugged test tubes having an inner diameter of 18 mm to prepare 13 test tubes containing a test tube medium for production. The ingredients used to prepare the test tube medium for production were obtained from lots where microbial cells had been confirmed not to grow well.

The 12 trace metals indicated in Table 1 were separately prepared in 0.8 ml volumes to have their final concentrations indicated in Table 1 and then added to the above 12 test tubes for production, respectively. The remaining one test tube was supplemented with 0.8 ml of ion exchanged water. The medium in each test tube was adjusted to pH 7.2 with aqueous sodium hydroxide or aqueous sulfuric acid, and then sterilized in an autoclave at 121° C. for 20 minutes.

*Paracoccus carotinifaciens* strain E-396 (FERM BP-4283) was inoculated into the test tube medium for seed culture and then cultured under shaking at 28° C. for 2 days at 300 spm. The resulting culture solution was then inoculated in 0.05 ml volumes into the 13 types of test tube media for production and cultured under shaking at 28° C. for 4 days at 300 spm.

When microbial cell growth after culture was determined by OD610, only the test tube supplemented with cobalt chloride hexahydrate was found to show good growth (Table 5).

TABLE 5

| Ingredient added | OD610 |
|---|---|
| Sodium molybdate dihydrate | 4 |
| Manganese sulfate pentahydrate | 5 |
| Sodium tungstate | 4 |
| Zinc sulfate heptahydrate | 5 |
| Nickel sulfate hexahydrate | 3 |
| Copper sulfate pentahydrate | 4 |
| Boric acid | 4 |
| Potassium iodide | 4 |
| Sodium selenate | 3 |
| Cobalt chloride hexahydrate | 32 |
| Aluminum (III) chloride hexahydrate | 4 |
| Chromium (III) chloride hexahydrate | 3 |
| Ion exchanged water | 4 |

Example 3

The same procedure as shown in Example 1 was repeated to prepare a test tube medium for seed culture. Subsequently, a medium of the following composition (glucose 30 g/L, filtered corn steep liquor 30 g/L, ammonium sulfate 1.5 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, silicon-based defoaming agent 0.2 g/L) was dispensed in 7.2 ml volumes into cotton-plugged test tubes having an inner diameter of 18 mm to prepare 12 test tubes containing a test tube medium for production. The ingredients used to prepare the test tube medium for production were obtained from lots where microbial cells had been confirmed not to grow well.

Cobalt chloride hexahydrate was added as an aqueous solution in 0.8 ml volumes to give final concentrations of 0, 0.0001, 0.001, 0.002, 0.005, 0.01, 0.1, 0.25, 1, 2, 5 and 10 mg/L (i.e., 0, 0.00042, 0.0042, 0.0084, 0.021, 0.042, 0.42, 1.1, 4.2, 8.4, 21 and 42 μmol/L) in the above 12 test tubes for production, respectively. The medium in each test tube was adjusted to pH 7.2 with aqueous sodium hydroxide or aqueous sulfuric acid, and then sterilized in an autoclave at 121° C. for 20 minutes.

*Paracoccus carotinifaciens* strain E-396 (FERM BP-4283) was inoculated into the test tube medium for seed culture and then cultured under shaking at 28° C. for 2 days at 300 spin. The resulting culture solution was then inoculated in 0.05 ml volumes into the 12 types of test tube media for production having different cobalt concentrations, and cultured under shaking at 28° C. for 4 days at 300 spm.

The cobalt concentration after seed inoculation in the above test tube medium for production free from cobalt chloride hexahydrate, which had been prepared separately, was found to be 0.002 μmol/L when measured by ICP-MS (Inductively Coupled Plasma-Mass Spectrometry). The cobalt concentration in the cobalt chloride-free medium and the concentration of cobalt chloride added to each medium were summed up to calculate the concentration of cobalt present in each medium (Table 6).

Figure 2:
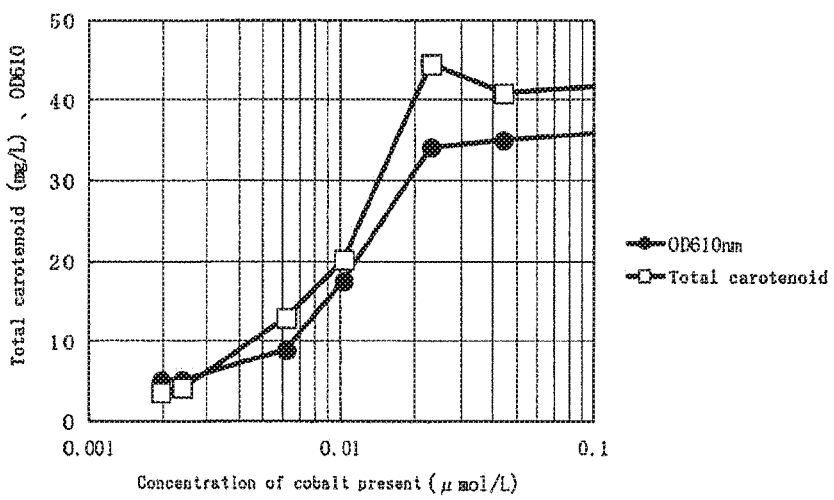
FIG. 2 shows the relationship between the concentration of cobalt present in a medium and microbial cell growth OD610 or total carotenoid production level, compared in the low concentration range (0.001 to 0.1 µmol/L).
Figure 3:
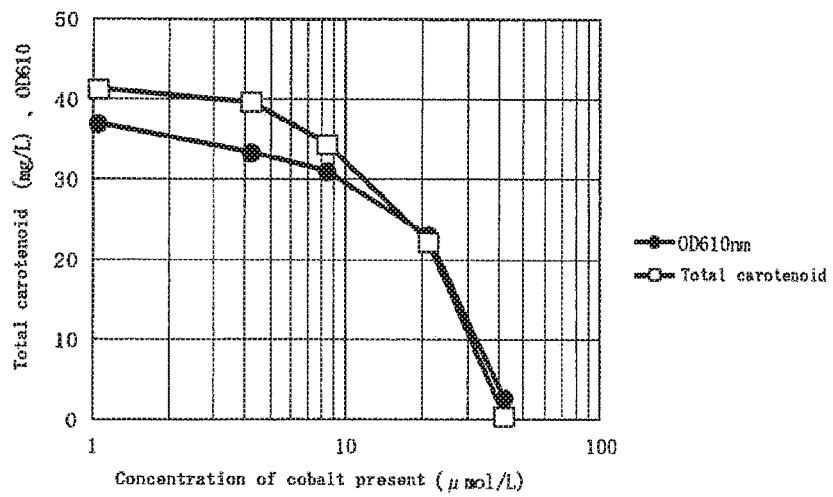
FIG. 3 shows the relationship between the concentration of cobalt present in a medium and microbial cell growth OD610 or total carotenoid production level, compared in the high concentration range (1 to 100 µmol/L).
Figure 4:
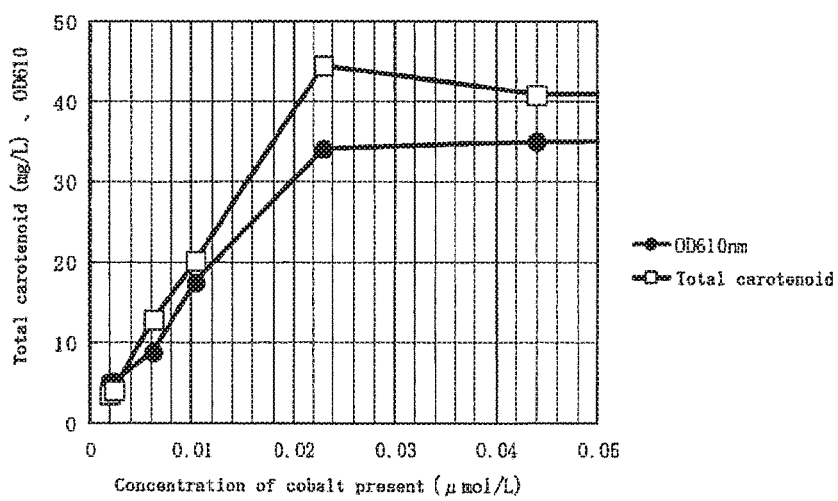
FIG. 4 shows the relationship between the concentration of cobalt present in a medium and microbial cell growth OD610 or total carotenoid production level, compared in the low concentration range (0 to 0.05 µmol/L).

After being cultured for 4 days, the culture solutions were each measured for microbial cell growth by OD610 and measure for carotenoid levels by HPLC. The results obtained are shown in Table 6. In addition, FIG. 1 shows the relationship between the concentration of cobalt present in the medium and microbial cell growth OD610 or total carotenoid production level. Moreover, FIGS. 2 to 4 show graphs plotted in enlarged scale for the high and low concentration ranges of cobalt present in the medium. FIGS. 2 to 4 indicated that an effective concentration range for carotenoid production was 0.005 μmol/L or higher and 8 μmol/L or lower, a more effective concentration range was 0.01 μmol/L or higher and 8 μmol/L or lower, and an even more effective concentration range was 0.02 μmol/L or higher and 8 μmol/L or lower.

When the cobalt concentration was too low, the number of bacterial cells and the yield of carotenoids were found to increase in a dose-dependent manner, while the number of bacterial cells and the yield of carotenoids were both found to decrease in a dose-dependent manner when the cobalt concentration was too high, thus indicating that there was an appropriate concentration range of cobalt for carotenoid production.

TABLE 6

| Concentration of cobalt added (μmol/L) | 0 | 0.00042 | 0.0042 | 0.0084 | 0.021 | 0.042 | 0.42 | 1.1 | 4.2 | 8.4 | 21 | 42 |
|---|---|---|---|---|---|---|---|---|---|---|---|---|
| Concentration of cobalt present (μmol/L) | 0.002 | 0.0024 | 0.0062 | 0.0104 | 0.023 | 0.044 | 0.42 | 1.05 | 4.2 | 8.4 | 21 | 42 |
| OD610 | 5 | 5 | 9 | 18 | 34 | 35 | 37 | 37 | 33 | 31 | 23 | 3 |
| Carotenoid (mg/L) | | | | | | | | | | | | |
| β-Carotene | 0.2 | 0.2 | 1.0 | 1.1 | 1.0 | 0.8 | 0.8 | 0.8 | 0.7 | 0.8 | 1.2 | 0.0 |
| Echinenone | 0.0 | 0.0 | 0.2 | 0.4 | 1.4 | 1.2 | 1.2 | 1.2 | 1.4 | 2.0 | 2.8 | 0.0 |
| 3-Hydroxyechinenone | 0.1 | 0.1 | 0.3 | 0.4 | 0.5 | 0.5 | 0.7 | 0.4 | 0.2 | 0.1 | 0.1 | 0.0 |
| Canthaxanthin | 0.0 | 0.0 | 0.1 | 0.9 | 3.4 | 2.6 | 2.3 | 3.1 | 8.1 | 9.9 | 9.4 | 0.1 |
| Adonirubin | 0.0 | 0.0 | 0.4 | 1.3 | 8.3 | 6.4 | 5.8 | 7.0 | 14.3 | 11.9 | 6.5 | 0.2 |
| Astaxanthin | 1.0 | 0.8 | 3.6 | 11.7 | 26.5 | 25.5 | 28.6 | 26.8 | 14.2 | 9.3 | 1.9 | 0.1 |
| Asteroidenone | 0.1 | 0.1 | 0.3 | 0.4 | 0.4 | 0.4 | 0.5 | 0.3 | 0.1 | 0.1 | 0.1 | 0.0 |
| Adonixanthin | 2.2 | 3.0 | 7.0 | 4.0 | 3.1 | 3.5 | 3.2 | 1.7 | 0.7 | 0.3 | 0.2 | 0.0 |
| Total carotenoid | 3.6 | 4.1 | 12.9 | 20.2 | 44.5 | 40.9 | 42.9 | 41.3 | 39.7 | 34.4 | 22.2 | 0.4 |

Example 4

The same procedure as shown in Example 1 was repeated to prepare a test tube medium for seed culture. Subsequently, medium ingredients from different manufacturers and lots were combined to prepare 5 types of media, i.e., A, B, C, D and E indicated in Table 7, each having the following composition (glucose 30 g/L, filtered corn steep liquor 30 g/L, ammonium sulfate 1.5 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, silicon-based defoaming agent 0.2 g/L). These media were each dispensed in 7.2 ml volumes into cotton-plugged test tubes having an inner diameter of 18 mm to prepare 2 test tubes for each test tube medium for production, i.e., 10 test tubes in total.

Cobalt chloride hexahydrate was then prepared as an aqueous solution in 0.8 ml volumes to give a final concentration of 0.1 mg/L (i.e., 0.42 μmol/L) and added to one test tube each of A, B, C, D and E, while the other test tubes were each supplemented with 0.8 ml of ion exchanged water as a negative control. The medium in each test tube was adjusted to pH 7.2 with aqueous sodium hydroxide or aqueous sulfuric acid, and then sterilized in an autoclave at 121° C. for 20 minutes.

*Paracoccus carotinifaciens* strain E-396 (FERM BP-4283) was inoculated into the test tube medium for seed culture and then cultured under shaking at 28° C. for 2 days at 300 spm. The resulting culture solution was then inoculated in 0.05 ml volumes into the 5 types of test tube media for production having different cobalt concentrations (10 test tubes in total), and cultured under shaking at 28° C. for 4 days at 300 spm.

Figure 5:
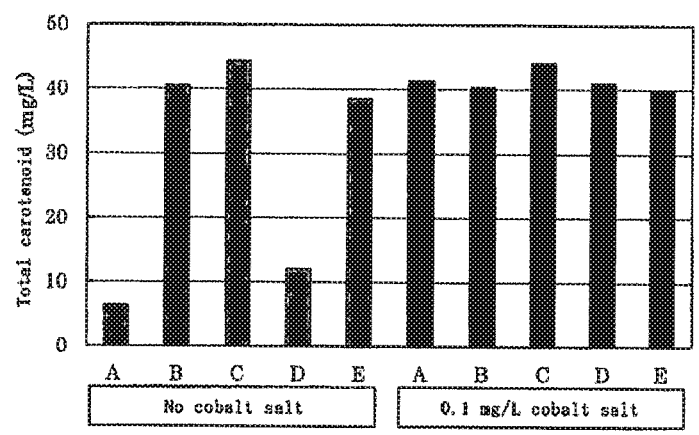
FIG. 5 shows differences in total carotenoid level among batches, measured in a cobalt chloride-supplemented medium and in a cobalt chloride-free medium.

After being cultured for 4 days, the culture solutions were each measured for microbial cell growth by OD610 and measure for carotenoid levels by HPLC. The results obtained in the absence of cobalt chloride (the cobalt concentration after seed inoculation in the test tube media for production free from cobalt chloride hexahydrate, which had been prepared separately, was measured by ICP-MS) are shown in Table 8, while the results obtained in the presence of cobalt chloride are shown in Table 9. In addition, a comparison of total carotenoid is shown in FIG. 5. In the absence of cobalt chloride, there were great variations in microbial cell growth and carotenoid production levels depending on the manufacturer and lot of each medium ingredient. In particular, the medium lots A and D where the concentration of cobalt present therein was low were found to show extremely low carotenoid production levels. In contrast, in the media supplemented with cobalt chloride at a final concentration of 0.1 mg/L, high bacterial growth and high carotenoid productivity were observed consistently, regardless of the manufacturer and lot of each medium ingredient, thus indicating the importance that the cobalt concentration in the medium should be within an appropriate range.

TABLE 7

| | Medium lot | | | | |
|---|---|---|---|---|---|
| | A | B | C | D | E |
| Glucose | Kishida Chemical | Kishida Chemical | Kishida Chemical | Wako Pure Chemical Industries | Wako Pure Chemical Industries |
| | G32834E | D48661 | M52359Y | APN7007 | ALG5549 |
| CSL | San-ei Sucrochemical | San-ei Sucrochemical | San-ei Sucrochemical | Showa Sangyo | Nihon Shokuhin Kako |
| | 9316 | 6717 | 6120 | 090518 | 12/9 |
| Ammonium sulfate | Junsei Chemical | Wako Pure Chemical Industries | Wako Pure Chemical Industries | Kanto Chemical | Kishida Chemical |
| | 2014C1198 | SEF2855 | DPM4971 | 206U1956 | F70879N |

TABLE 7-continued

|  | Medium lot | | | | |
| --- | --- | --- | --- | --- | --- |
|  | A | B | C | D | E |
| Potassium dihydrogen phosphate | Kanto Chemical 306U1707 | Junsei Chemical 2013L1259 | Junsei Chemical 2013G1079 | Kishida Chemical C25853S | Kishida Chemical F28125S |
| Disodium hydrogen phosphate dodecahydrate | Kanto Chemical 511H1795 | Kishida Chemical F16627R | Kishida Chemical L09786P | Kishida Chemical A31014X | Wako Pure Chemical Industries PDN2839 |
| Calcium chloride dihydrate | Junsei Chemical 2014D1170 | Junsei Chemical 2013D1266 | Wako Pure Chemical Industries WAN2082 | Wako Pure Chemical Industries STE3818 | Kishida Chemical M22598R |
| Magnesium sulfate heptahydrate | Kanto Chemical 608H1524 | Kanto Chemical 604H1834 | Kishida Chemical H75356N | Junsei Chemical 2B1020 | Wako Pure Chemical Industries LTN7694 |
| Iron sulfate heptahydrate | Wako Pure Chemical Industries PTF2135 | Junsei Chemical 2013G1485 | Kishida Chemical C35842L | Kishida Chemical L15782C | Kishida Chemical G12048C |

TABLE 8

Concentration of cobalt chloride added
0 mg/L

| | Medium lot | | | | | | |
| --- | --- | --- | --- | --- | --- | --- | --- |
| | A | B | C | D | E | | |
| | Total cobalt concentration (μmol/L) | | | | | | |
| | 0.002 | 0.20 | 0.042 | 0.006 | 0.067 | Average | SD |
| OD610 | 6 | 36 | 37 | 8 | 35 | 24 | 16 |
| Astaxanthin (mg/L) | 2 | 28 | 29 | 4 | 26 | 18 | 14 |
| Total carotenoid (mg/L) | 6 | 40 | 44 | 12 | 39 | 28 | 18 |

TABLE 9

Concentration of cobalt chloride added
0.1 mg/L (0.42 μmol/L)

| | Medium lot | | | | | | |
| --- | --- | --- | --- | --- | --- | --- | --- |
| | A | B | C | D | E | | |
| | Total cobalt concentration (μmol/L) | | | | | | |
| | 0.42 | 0.62 | 0.46 | 0.43 | 0.49 | Average | SD |
| OD610 | 37 | 39 | 38 | 36 | 37 | 37 | 1.1 |
| Astaxanthin (mg/L) | 29 | 26 | 29 | 27 | 28 | 28 | 1.2 |
| Total carotenoid (mg/L) | 41 | 40 | 44 | 41 | 40 | 41 | 1.7 |

Example 5

*Paracoccus carotinifaciens* strain E-396 was mutated with N-methyl-N'-nitro-N-nitrosoguanidine and cultured in a test tube medium containing 0.4 mmol/L clomazone for 10 days. This culture solution was applied onto an agar medium containing 0.3 mmol/L fosmydomycin and cultured thereon to select colonies with a darker red color tone. The selected strains were analyzed for carotenoids in their culture solutions to select a mutant strain CF-358 with improved astaxanthin productivity.

A medium of the following composition (glucose 20 g/L, filtered corn steep liquor 5 g/L, potassium dihydrogen phosphate 0.54 g/L, dipotassium hydrogen phosphate 2.78 g/L, calcium chloride dihydrate 5.0 g/L, magnesium sulfate heptahydrate 0.7 g/L, iron sulfate heptahydrate 1.0 g/L, alcohol-based defoaming agent 0.2 g/L, pH 7.5) was dispensed in 100 ml volumes into 500 ml cotton-plugged Erlenmeyer flasks and sterilized in an autoclave at 121° C. for 20 minutes to prepare 5 flasks containing a seed flask medium. The ingredients used to prepare the seed flask medium were obtained from lots where microbial cells had been confirmed to grow well.

Subsequently, a medium of the following composition (glucose 40 g/L, filtered corn steep liquor 30 g/L, ammonium sulfate 0.5 g/L, sodium glutamate monohydrate 6 g/L, potassium dihydrogen phosphate 2.25 g/L, disodium hydrogen phosphate dodecahydrate 5.7 g/L, calcium chloride dihydrate 0.1 g/L, magnesium sulfate heptahydrate 0.5 g/L, iron sulfate heptahydrate 1.0 g/L, biotin 0.1 mg/L, alcohol-based defoaming agent 0.5 g/L) was dispensed in 2.0 L volumes into 5 L fermenters to prepare 5 fermenters containing a production medium.

Cobalt chloride hexahydrate was added to give final concentrations of 0, 0.01, 0.1, 1 and 5 mg/L (i.e., 0, 0.042, 0.42, 4.2 and 21 μmol/L) in the above fermenters for production. The medium in each fermenter was sterilized in an autoclave at 121° C. for 30 minutes, cooled and then adjusted to pH 7.2 with 20% aqueous sodium hydroxide. The cobalt concentration after seed inoculation in the cobalt chloride-free fermenter medium was found to be 0.003 μmol/L when measured by ICP-MS.

The *Paracoccus carotinifaciens* mutant strain CF-358 selected as above was inoculated into the seed flask medium, followed by rotary shaking culture at 28° C. for 2 days at 100 rpm. The resulting culture solution was then inoculated in 80 ml volumes into the individual fermenters, followed by aeration spinner culture at 28° C. under a gauge pressure of 0.01 MPa at an aeration volume of 1.5 vvm for 5 days. To maintain a pH of 7.2 during culture, 15% aqueous ammonia was automatically supplied. The number of spinner rotations was automatically varied such that the dissolved oxygen concentration in each culture solution was maintained at 2 to 4 ppm. An alcohol-based defoaming agent was automatically added to avoid bubbling.

At the completion of culture, the culture solutions were each measured for microbial cell growth by OD610 and measured for carotenoid levels by HPLC (Table 10). The fermenters supplemented with cobalt chloride at a final concentration of 0.042 to 21 μmol/L were found to show high total carotenoid production level. In contrast, in the absence of cobalt chloride, the total carotenoid production level was low.

TABLE 10

| Concentration of cobalt added (μmol/L) | 0 | 0.042 | 0.42 | 4.2 | 21 |
|---|---|---|---|---|---|
| Total cobalt concentration in medium (μmol/L) | 0.003 | 0.045 | 0.42 | 4.2 | 21 |
| OD610 | 28 | 194 | 208 | 191 | 143 |
| Carotenoid (mg/L) | | | | | |
| β-Carotene | 6 | 58 | 60 | 29 | 27 |
| Echinenone | 3 | 37 | 37 | 61 | 103 |
| 3-Hydroxyechinenone | 3 | 12 | 12 | 5 | 4 |
| Canthaxanthin | 3 | 90 | 74 | 338 | 431 |
| Adonirubin | 7 | 273 | 216 | 285 | 347 |
| Astaxanthin | 61 | 775 | 815 | 580 | 103 |
| Asteroidenone | 2 | 11 | 15 | 3 | 1 |
| Adonixanthin | 50 | 45 | 73 | 18 | 7 |
| Total carotenoid | 135 | 1302 | 1303 | 1319 | 1023 |
| Total carotenoid/dry microbial cells (mg/g) | 30.7 | 41.9 | 39.1 | 43.2 | 44.9 |

Example 6

A medium of the following composition (sucrose 30 g/L, corn steep liquor 30 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1 g/L, pH 7.2) was dispensed in 8 ml volumes into cotton-plugged test tubes having an inner diameter of 18 mm and sterilized in an autoclave at 121° C. for 15 minutes to prepare a test tube medium for seed culture. The ingredients used to prepare the test tube medium for seed culture were obtained from lots where microbial cells had been confirmed to grow well.

Subsequently, a medium of the following composition (glucose 40 g/L, potassium dihydrogen phosphate 0.54 g/L, dipotassium hydrogen phosphate 2.78 g/L, ammonium sulfate 1.5 g/L, calcium chloride dihydrate 1 g/L, sodium chloride 3 g/L, magnesium sulfate heptahydrate 0.7 g/L, iron sulfate heptahydrate 0.5 g/L, manganese sulfate pentahydrate 5 mg/L, boric acid 5 mg/L, zinc sulfate heptahydrate 5 mg/L, sodium molybdate dihydrate 2 mg/L, copper sulfate pentahydrate 2 mg/L, potassium iodide 1 mg/L, sodium tungstate 1 mg/L, nickel sulfate hexahydrate 1 mg/L, sodium selenate 0.1 mg/L, aluminum (III) chloride hexahydrate 0.1 mg/L, chromium (III) chloride hexahydrate 0.1 mg/L, myo-inositol 50 mg/L, ascorbic acid 30 mg/L, pyridoxine hydrochloride 20 mg/L, calcium pantothenate 15 mg/L, riboflavin 10 mg/L, p-aminobenzoic acid 10 mg/L, choline 10 mg/L, cyanocobalamin 5 mg/L, thiamine hydrochloride 1 mg/L, folic acid 1 mg/L, niacin 1 mg/L, biotin 0.1 mg/L, polyether-based defoaming agent 0.2 g/L) was dispensed in 7.2 ml volumes into cotton-plugged test tubes having an inner diameter of 18 mm to prepare 7 test tubes containing a test tube medium for production. The ingredients used to prepare the test tube medium for production were obtained from lots where microbial cells had been confirmed not to grow well.

Cobalt chloride hexahydrate was prepared as an aqueous solution in 0.8 ml volumes to give final concentrations of 0, 0.0001, 0.001, 0.01, 0.1, 1 and 10 mg/L (i.e., 0, 0.00042, 0.0042, 0.042, 0.42, 4.2 and 42 μmol/L) and added to the above test tubes for production, respectively. The medium in each test tube was adjusted to pH 7.2 with aqueous sodium hydroxide or aqueous sulfuric acid, and then sterilized in an autoclave at 121° C. for 20 minutes.

*Paracoccus* sp. strain A-581-1 (FERM BP-4671) was inoculated into the test tube medium for seed culture and then cultured under shaking at 29° C. for 2 days at 300 spm. The resulting culture solution was then inoculated in 0.05 ml volumes into the 7 types of test tube media for production having different cobalt concentrations, and cultured under shaking at 29° C. for 4 days at 300 spm.

The cobalt concentration after seed inoculation in the test tube medium for production free from cobalt chloride hexahydrate, which had been prepared separately, was found to be 0.002±mol/L when measured by ICP-MS.

After being cultured for 4 days, the culture solutions were each measured for microbial cell growth by OD610 and measure for carotenoid levels by HPLC. The results obtained are shown in Table 11 along with the total concentration of cobalt in the medium. *Paracoccus* sp. strain A-581-1, which had been discovered by being isolated from soil independently of the strain E-396, also showed extremely low growth and low carotenoid production at either too low or too high a cobalt concentration, as in the case of the strain E-396.

TABLE 11

| Concentration of cobalt added (μmol/L) | 0 | 0.00042 | 0.0042 | 0.042 | 0.42 | 4.2 | 42 |
|---|---|---|---|---|---|---|---|
| Total cobalt concentration (μmol/L) | 0.0020 | 0.0024 | 0.0062 | 0.044 | 0.42 | 4.2 | 42 |
| OD610 | 3 | 3 | 5 | 21 | 22 | 21 | 2 |
| Astaxanthin (mg/L) | 0.2 | 0.3 | 0.5 | 2.0 | 2.1 | 1.2 | 0.0 |
| Total carotenoid (mg/L) | 0.8 | 0.9 | 1.7 | 5.3 | 5.6 | 5.5 | 0.2 |

Example 7

The same procedure as shown in Example 1 was repeated to prepare a test tube medium for seed culture. Subsequently, a medium of the following composition (glucose 30 g/L, filtered corn steep liquor 30 g/L, ammonium sulfate 1.5 g/L, potassium dihydrogen phosphate 1.5 g/L, disodium hydrogen phosphate dodecahydrate 3.8 g/L, calcium chloride dihydrate 5.0 g/L, magnesium sulfate heptahydrate 0.7 g/L, iron sulfate heptahydrate 1.0 g/L, silicon-based defoaming agent 0.2 g/L) was dispensed in 7.2 ml volumes into cotton-plugged test tubes having an inner diameter of 18 mm to prepare 9 test tubes containing a test tube medium for production. The ingredients used to prepare the test tube medium for production were obtained from lots where microbial cells had been confirmed not to grow well.

Cobalt chloride hexahydrate was prepared as an aqueous solution in 0.8 ml volumes to give final concentrations of 0, 0.0001, 0.001, 0.005, 0.01, 0.1, 1, 5 and 10 mg/L (i.e., 0, 0.00042, 0.0042, 0.021, 0.042, 0.42, 4.2, 21 and 42 μmol/L)

and added to the above 9 test tubes for production, respectively. The medium in each test tube was adjusted to pH 7.2 with aqueous sodium hydroxide or aqueous sulfuric acid, and then sterilized in an autoclave at 121° C. for 20 minutes.

*Paracoccus zeaxanthinifaciens* strain ATCC 21588 was inoculated into the test tube medium for seed culture and then cultured under shaking at 28° C. for 2 days at 300 spm. The resulting culture solution was then inoculated in 0.05 ml volumes into the 9 types of test tube media for production having different cobalt concentrations, and cultured under shaking at 28° C. for 4 days at 300 spm.

The cobalt concentration after seed inoculation in the test tube medium for production free from cobalt chloride hexahydrate, which had been prepared separately, was found to be 0.002 μmol/L when measured by ICP-MS.

After being cultured for 4 days, the culture solutions were each measured for microbial cell growth by OD610 and measure for carotenoid levels by HPLC. The results obtained are shown in Table 12. This strain showed extremely low growth and low carotenoid production at either too low or too high a cobalt concentration, thus indicating that the concentration range of cobalt suitable for production of zeaxanthin and β-cryptoxanthin in *Paracoccus zeaxanthinifaciens* was the same as in other bacteria of the genus *Paracoccus*.

TABLE 12

| | | | | | | | | |
|---|---|---|---|---|---|---|---|---|
| Concentration of cobalt added (μmol/L) | 0 | 0.00042 | 0.0042 | 0.021 | 0.042 | 0.42 | 4.2 | 21 | 42 |
| Total cobalt concentration (μmol/L) | 0.0020 | 0.0024 | 0.0062 | 0.023 | 0.044 | 0.42 | 4.2 | 21 | 42 |
| OD610 | 2 | 2 | 6 | 25 | 29 | 29 | 28 | 24 | 18 |
| Carotenoid (mg/L) | | | | | | | | | |
| β-Carotene | 0.0 | 0.0 | 0.2 | 0.7 | 0.8 | 0.7 | 0.7 | 0.6 | 0.3 |
| β-Cryptoxanthin | 0.0 | 0.0 | 0.1 | 0.3 | 0.3 | 0.3 | 0.3 | 0.4 | 0.3 |
| Zeaxanthin | 0.5 | 0.6 | 2.0 | 10.6 | 13.6 | 13.4 | 12.9 | 10.8 | 6.4 |
| Total carotenoid | 0.5 | 0.6 | 2.3 | 11.6 | 14.7 | 14.4 | 13.9 | 11.8 | 7.0 |

Sequence Listing Free Text n represents a, c, g or t (Location: 1350).

The invention claimed is:

1. A method for stable preparation of microbial cells containing carotenoids in an amount of at least 36 mg/g in dry microbial cells, comprising culturing bacteria belonging to the genus *Paracoccus* in a medium containing cobalt or a cobalt salt at a concentration of 0.005 μmol/L to 7 μmol/L, wherein the culturing step is carried out by aeration spinner culture.

2. The method of claim 1, wherein the cobalt or cobalt salt has been added at a concentration of 0.005 μmol/L to 7 μmol/L in the medium.

3. The method according to claim 1, wherein the carotenoids comprise at least one selected from the group consisting of astaxanthin, canthaxanthin, zeaxanthin, β-cryptoxanthin, lycopene, β-carotene, adonirubin, adonixanthin, echinenone, asteroidenone and 3-hydroxyechinenone.

4. The method according to claim 1, wherein the bacteria belonging to the genus *Paracoccus* are those comprising DNA which corresponds to 16S ribosomal RNA and whose nucleotide sequence shares a homology of 95% or higher with the nucleotide sequence shown in SEQ ID NO: 1.

5. The method according to claim 1, wherein the bacteria belonging to the genus *Paracoccus* are those of the strain E-396 (FERM BP-4283) or the strain A-581-1 (FERM BP-4671) or a mutant strain thereof.

6. A method for production of carotenoids, comprising culturing bacteria belonging to the genus *Paracoccus* in a medium containing cobalt or a cobalt salt at a concentration of 0.005 μmol/L to 7 μmol/L to thereby obtain microbial cells containing carotenoids in an amount of at least 36 mg/g in dry microbial cells, and collecting the carotenoids from the cultured product containing the microbial cells, wherein the culturing step is carried out by aeration spinner culture.

7. The method of claim 6, wherein the cobalt or cobalt salt has been added at a concentration of 0.005 μmol/L to 7 μmol/L in the medium.

8. The method according to claim 6, wherein the carotenoids comprise at least one selected from the group consisting of astaxanthin, canthaxanthin, zeaxanthin, β-cryptoxanthin, lycopene, β-carotene, adonirubin, adonixanthin, echinenone, asteroidenone and 3-hydroxyechinenone.

9. The method according to claim 6, wherein the bacteria belonging to the genus *Paracoccus* are those comprising DNA which corresponds to 16S ribosomal RNA and whose nucleotide sequence shares a homology of 95% or higher with the nucleotide sequence shown in SEQ ID NO: 1.

10. The method according to claim 6, wherein the bacteria belonging to the genus *Paracoccus* are those of the strain E-396 (FERM BP-4283) or the strain A-581-1 (FERM BP-4671) or a mutant strain thereof.

11. A method for stabilization of carotenoid levels in microbial cells such that carotenoids are contained in an amount of at least 36 mg/g in dry microbial cells, comprising culturing bacteria belonging to the genus *Paracoccus* in a medium containing cobalt or a cobalt salt at a concentration of 0.005 μmol/L to 7 μmol/L, wherein the culturing step is carried out by aeration spinner culture.

12. The method of claim 11, wherein the cobalt or cobalt salt has been added at a concentration of 0.005 μmol/L to 7 μmol/L in the medium.

13. The method according to claim 11, wherein the carotenoids comprise at least one selected from the group consisting of astaxanthin, canthaxanthin, zeaxanthin, β-cryptoxanthin, lycopene, β-carotene, adonirubin, adonixanthin, echinenone, asteroidenone and 3-hydroxyechinenone.

14. The method according to claim 11, wherein the bacteria belonging to the genus *Paracoccus* are those comprising DNA which corresponds to 16S ribosomal RNA and whose nucleotide sequence shares a homology of 95% or higher with the nucleotide sequence shown in SEQ ID NO: 1.

15. The method according to claim 11, wherein the bacteria belonging to the genus *Paracoccus* are those of the strain E-396 (FERM BP-4283) or the strain A-581-1 (FERM BP-4671) or a mutant strain thereof.

16. The method of claim 1, wherein the bacteria belonging to the genus *Paracoccus* are at least one selected from the group consisting of *Paracoccus carotinifaciens*, *Paracoccus marcusii*, *Paracoccus haeundaensis* and *Paracoccus zeaxanthinifaciens*.

17. The method of claim 6, wherein the bacteria belonging to the genus *Paracoccus* are at least one selected from the group consisting of *Paracoccus carotinifaciens, Paracoccus marcusii, Paracoccus haeundaensis* and *Paracoccus zeaxanthinifaciens.*

18. The method of claim 11, wherein the bacteria belonging to the genus *Paracoccus* are at least one selected from the group consisting of *Paracoccus carotinifaciens, Paracoccus marcusii, Paracoccus haeundaensis* and *Paracoccus zeaxanthinifaciens.*

\* \* \* \* \*